US011331003B2

(12) United States Patent
Rahman et al.

(10) Patent No.: US 11,331,003 B2
(45) Date of Patent: May 17, 2022

(54) CONTEXT-AWARE RESPIRATION RATE DETERMINATION USING AN ELECTRONIC DEVICE

(71) Applicant: Samsung Electronics Co., Ltd, Suwon-si (KR)

(72) Inventors: Md Mahbubur Rahman, Sunnyvale, CA (US); Ebrahim Nemati, Santa Clara, CA (US); Jilong Kuang, San Jose, CA (US); Nasson Boroumand, Gold River, CA (US); Jun Gao, Menlo Park, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 538 days.

(21) Appl. No.: 16/049,743

(22) Filed: Jul. 30, 2018

(65) Prior Publication Data
US 2019/0298224 A1    Oct. 3, 2019

Related U.S. Application Data

(60) Provisional application No. 62/648,750, filed on Mar. 27, 2018.

(51) Int. Cl.
*A61B 5/08* (2006.01)
*A61B 5/0205* (2006.01)
(Continued)

(52) U.S. Cl.
CPC .......... *A61B 5/0816* (2013.01); *A61B 5/0205* (2013.01); *A61B 5/0803* (2013.01);
(Continued)

(58) Field of Classification Search
CPC ... A61B 5/0816; A61B 5/0205; A61B 5/0803; A61B 5/725; A61B 5/02416;
(Continued)

(56) References Cited

U.S. PATENT DOCUMENTS

2008/0139955 A1    6/2008   Hansmann et al.
2009/0157584 A1    6/2009   Yang et al.
(Continued)

FOREIGN PATENT DOCUMENTS

JP    2015-531261 A    11/2015
JP    2018-506763 A     3/2018
(Continued)

OTHER PUBLICATIONS

International Search Report dated Oct. 31, 2019 in connection with International Patent Application No. PCT/KR2019/009413, 3 pages.
(Continued)

*Primary Examiner* — Andrey Shostak

(57) ABSTRACT

A method for contextually aware determination of respiration includes obtaining, by an electronic device, context information and selecting, by the electronic device, a set of sensor data associated with respiratory activity of a subject, based on the context information. The method further includes selecting, based on the selected set of sensor data, an algorithm from a plurality of algorithms for determining a respiration rate of the subject, and determining, by applying the selected algorithm to the selected set of sensor data associated with respiratory activity of the subject, the respiration rate for the subject.

20 Claims, 9 Drawing Sheets

(51) Int. Cl.
*A61B 5/00* (2006.01)
*G16H 50/20* (2018.01)
*A61B 5/024* (2006.01)

(52) U.S. Cl.
CPC .......... *A61B 5/725* (2013.01); *A61B 5/02416* (2013.01); *A61B 5/7278* (2013.01); *G16H 50/20* (2018.01)

(58) Field of Classification Search
CPC . A61B 5/7278; A61B 5/7267; A61B 5/14551; A61B 5/1135; A61B 5/6898; G16H 50/20; G16H 50/70
See application file for complete search history.

(56) References Cited

U.S. PATENT DOCUMENTS

| | | | |
|---|---|---|---|
| 2011/0257489 A1 | 10/2011 | Banet et al. | |
| 2012/0083705 A1* | 4/2012 | Yuen | A61B 5/743 |
| | | | 600/508 |
| 2013/0072145 A1* | 3/2013 | Dantu | A61B 7/003 |
| | | | 455/404.1 |
| 2013/0267862 A1 | 10/2013 | Jaffe et al. | |
| 2015/0250426 A1 | 9/2015 | Muehlsteff | |
| 2016/0066829 A1 | 3/2016 | Sales et al. | |
| 2016/0128638 A1* | 5/2016 | Altini | G16Z 99/00 |
| | | | 600/484 |
| 2016/0143557 A1* | 5/2016 | Kahlman | A61B 5/7228 |
| | | | 600/407 |
| 2016/0169930 A1 | 6/2016 | Korhonen et al. | |
| 2017/0042470 A1* | 2/2017 | Prerau | G06K 9/00536 |
| 2017/0071537 A1 | 3/2017 | Jain et al. | |
| 2017/0209055 A1* | 7/2017 | Pantelopoulos | A61B 5/02108 |
| 2017/0209074 A1* | 7/2017 | Siu | A61B 5/7235 |
| 2018/0028080 A1* | 2/2018 | Ouwerkerk | A61B 5/7207 |
| 2018/0055453 A1 | 3/2018 | Lee et al. | |
| 2018/0285528 A1* | 10/2018 | Healey | G06N 20/00 |
| 2019/0223782 A1* | 7/2019 | Wen | A61B 5/0816 |
| 2019/0294243 A1* | 9/2019 | Laszlo | G06F 3/015 |

FOREIGN PATENT DOCUMENTS

| | | |
|---|---|---|
| KR | 10-2008-0054855 A | 6/2008 |
| KR | 10-2016-0035120 A | 9/2014 |
| KR | 10-2017-0083909 A | 7/2017 |

OTHER PUBLICATIONS

Written Opinion of the International Searching Authority dated Oct. 31, 2019 in connection with International Patent Application No. PCT/KR2019/009413, 3 pages.

Supplementary European Search Report dated May 17, 2021 in connection with European Application No. 19843212.2, 8 pages.

* cited by examiner

CONTEXT-AWARE RESPIRATION RATE DETERMINATION USING AN ELECTRONIC DEVICE

CROSS-REFERENCE TO RELATED APPLICATION AND CLAIM OF PRIORITY

This application claims priority under 35 U.S.C. § 119(e) to U.S. Provisional Patent Application No. 62/648,750 filed on Mar. 27, 2018. The above-identified provisional patent application is hereby incorporated by reference in its entirety.

TECHNICAL FIELD

This disclosure relates generally to health measurement technology. More specifically, this disclosure relates to context-aware respiration rate determination using one or more electronic devices.

BACKGROUND

Respiration rate, or the number of breaths a person takes per minute, can be a highly effective datum as to a person's cardiopulmonary health, and in the case of patients with conditions such as Chronic Obstructive Pulmonary Disease (COPD), an early indicator of a potentially fatal deterioration of a patient's condition. Additionally, when used in conjunction with other metrics of cardiopulmonary condition, such as oxygen saturation ($SpO_2$), respiration rate can provide nuanced information as to a patient's cardiopulmonary health.

Smart electronic devices, such as smart mobile phones, which can include a variety of sensors (for example, microphones and motion measuring sensors), have become widely available, and for many people, indispensable lifestyle accessories which are worn all day. From a clinical perspective, measuring respiration rate with a device that is portable and consistently carried by a person, presents significant opportunities for early detection and treatment of otherwise significant, or even fatal, cardiopulmonary events. However, the implementation of such measurement techniques presents a number of technical challenges, including, without limitation, variation in the effectiveness of a device's sensors across measurement contexts.

SUMMARY

This disclosure provides systems and methods for context-aware respiration rate determination using one or more electronic devices.

In a first embodiment, a method for contextually aware respiration determination includes obtaining, by an electronic device, context information and selecting, by the electronic device, a set of sensor data associated with respiratory activity of a subject, based on the context information. The method further includes selecting, based on the selected set of sensor data, an algorithm from a plurality of algorithms for determining a respiration rate of the subject, and determining, by applying the selected algorithm to the selected set of sensor data associated with respiratory activity of the subject, the respiration rate for the subject.

In a second embodiment, an apparatus includes a processor, one or more sensors coupled to the processor, configured to capture one or more sets of sensor data and a memory. The memory contains computer-readable program code, which when executed by the processor, causes the apparatus to obtain context information, and select a set of sensor data associated with respiratory activity of a subject, based on the context information. The memory also contains computer-readable program code, which when executed by the processor, causes the apparatus to select, based on the selected set of sensor data, an algorithm from a plurality of algorithms for determining a respiration rate of the subject and determine, by applying the selected algorithm to the selected set of sensor data associated with respiratory activity of the subject, the respiration rate for the subject.

In a third embodiment, a non-transitory computer-readable medium includes program code, which when executed by a processor, causes an apparatus to obtain context information and select a set of sensor data associated with respiratory activity of a subject, based on the context information. Additionally, the non-transitory computer-readable medium includes program code, which when executed by the processor, causes the apparatus to select, based on the selected set of sensor data, an algorithm from a plurality of algorithms for determining a respiration rate of the subject and determine, by applying the selected algorithm to the selected set of sensor data associated with respiratory activity of the subject, the respiration rate for the subject.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many, if not most instances, such definitions apply to prior as well as future uses of such defined words and phrases.

BRIEF DESCRIPTION OF THE DRAWINGS

For a more complete understanding of this disclosure and its advantages, reference is now made to the following description, taken in conjunction with the accompanying drawings, in which.

DETAILED DESCRIPTION

FIGS. 1 through 9, discussed below, and the various embodiments used to describe the principles of this disclosure in this patent document are by way of illustration only and should not be construed in any way to limit the scope of the disclosure. Those skilled in the art will understand that the principles of this disclosure may be implemented in any suitably arranged wireless communication system.

Figure 1:
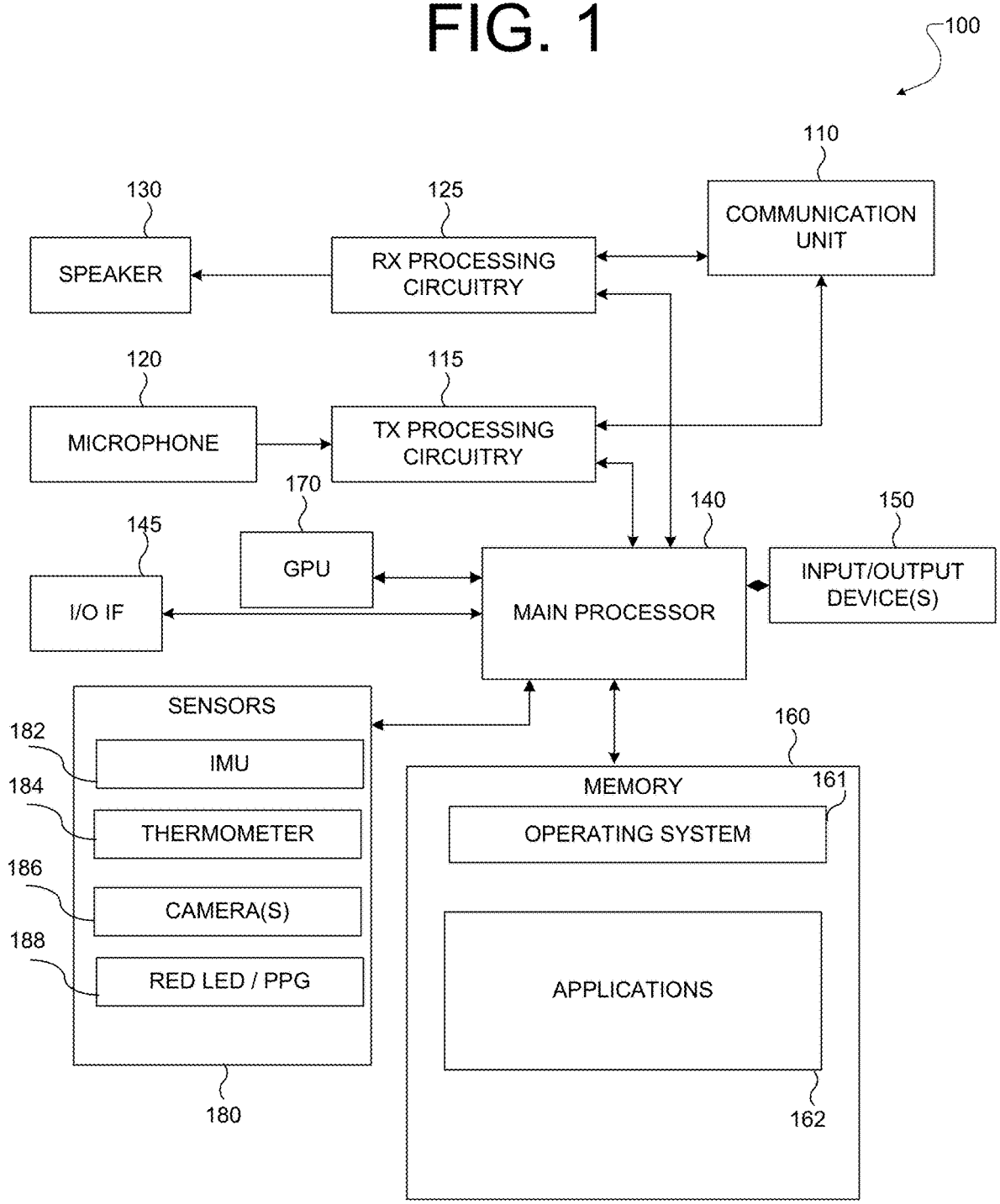
FIG. 1 illustrates an example of an electronic device in which various embodiments according to the present disclosure can be implemented.

FIG. 1 illustrates an example of a device 100 for implementing contextually aware determination of a respiration rate according to this disclosure. The embodiment of device 100 illustrated in FIG. 1 is for illustration only, and other configurations are possible. However, suitable devices come in a wide variety of configurations, and FIG. 1 does not limit the scope of this disclosure to any particular implementation of a device.

As shown in the non-limiting example of FIG. 1, the device 100 includes a communication unit 110 that may include, for example, a radio frequency (RF) transceiver, a Bluetooth® transceiver, or a Wi-Fi® transceiver, etc., transmit (TX) processing circuitry 115, a microphone 120, and receive (RX) processing circuitry 125. The device 100 also includes a speaker 130, a main processor 140, an input/output (I/O) interface (IF) 145, input/output device(s) 150, and a memory 160. The memory 160 includes an operating system (OS) program 161 and one or more applications 162.

Applications 162 can include games, health monitoring applications, virtual reality (VR) applications, augmented reality (AR) applications, operating systems, device security (e.g., anti-theft and device tracking) applications or any other applications for which a user's respiration rate constitutes relevant data. Additionally, applications 162 can, according to embodiments, output respiration rate information on an input/output device 150 as part of a display on a screen.

The communication unit 110 may receive an incoming RF signal, for example, a near field communication signal such as a BLUETOOTH® or Wi-Fi® signal. The communication unit 110 may down-convert the incoming RF signal to generate an intermediate frequency (IF) or baseband signal. The IF or baseband signal is sent to the RX processing circuitry 125, which generates a processed baseband signal by filtering, decoding, or digitizing the baseband or IF signal. The RX processing circuitry 125 transmits the processed baseband signal to the speaker 130 (such as for voice data) or to the main processor 140 for further processing (such as for web browsing data, online gameplay data, notification data, or other message data).

The TX processing circuitry 115 receives analog or digital sound that includes breathing or voice data from the microphone 120 or other outgoing baseband data (such as web data, e-mail, or interactive video game data) from the main processor 140. The TX processing circuitry 115 encodes, multiplexes, or digitizes the outgoing baseband data to generate a processed baseband or IF signal. The communication unit 110 receives the outgoing processed baseband or IF signal from the TX processing circuitry 115 and up-converts the baseband or IF signal to an RF signal for transmission.

The main processor 140 can include one or more processors or other processing devices and execute the OS program 161 stored in the memory 160 in order to control the overall operation of the device 100. For example, the main processor 140 could control the reception of forward channel signals and the transmission of reverse channel signals by the communication unit 110, the RX processing circuitry 125, and the TX processing circuitry 115 in accordance with well-known principles. In some embodiments, the main processor 140 includes at least one microprocessor or microcontroller.

The main processor 140 is also capable of executing other processes and programs resident in the memory 160. The main processor 140 can move data into or out of the memory 160 as required by an executing process. In some embodiments, the main processor 140 is configured to execute the applications 162 based on the OS program 161 or in response to inputs from a user, sensors 180 or applications 162. Applications 162 can include applications specifically developed for the platform of device 100, or legacy applications developed for earlier platforms. The main processor 140 is also coupled to the I/O interface 145, which provides the device 100 with the ability to connect to other devices such as laptop computers and handheld computers. The I/O interface 145 is the communication path between these accessories and the main processor 140.

The main processor 140 is also coupled to the input/output device(s) 150. The operator of the device 100 can use the input/output device(s) 150 to enter data into the device 100. Input/output device(s) 150 can include keyboards, touch screens, mouse(s), track balls or other devices capable of acting as a user interface to allow a user to interact with electronic device 100. In some embodiments, input/output device(s) 150 can include a touch panel, a heart rate monitor, a smartwatch, or a device for obtaining photoplethysomographic (PPG) data, a virtual reality headset, a (digital) pen sensor, a key, or an ultrasonic input device. Input/output device(s) 150 are, according to certain embodiments, associated with one or more of sensor(s) 180 to provide input to main processor 140.

Input/output device(s) 150 can include one or more screens, which can be a liquid crystal display, light-emitting diode (LED) display, an optical LED (OLED), an active matrix OLED (AMOLED), or other screens capable of rendering graphics.

The memory 160 is coupled to the main processor 140. According to certain embodiments, part of the memory 160 includes a random access memory (RAM), and another part of the memory 160 includes a Flash memory or other read-only memory (ROM). Although FIG. 1 illustrates one example of a device 100. Various changes can be made to FIG. 1.

For example, according to certain embodiments, device 100 can further include a separate graphics processing unit (GPU) 170, and sensors 180.

Sensors 180 can comprise a variety of sensors for generating inputs processed by device 100, and include without limitation, accelerometers, barometric pressure sensors, inertial measurement units (IMUs), digital cameras, touch sensors, digital thermometers, pressure sensors and global positioning system sensors. For example, sensors 180 can include an inertial measurement unit 182. Inertial measurement unit 182 can be an optical sensor, an accelerometer or a gyroscopic sensor. Additionally, inertial measurement unit 182 can comprise a plurality of IMUs, such as motion detectors coupled to a user's head or limbs. Additionally, sensors 180 may include a thermometer 184, camera 186, and sensors 188 (for example, a red LED) for performing photoplethysmography measurements. Camera 186 can be multiple cameras disposed on the exterior of the device to capture external image data, such as cameras for providing an augmented reality (AR) experience, in which digital images are superimposed over the view of a camera positioned on or near a user's eye. Camera 186 can also be any suitable camera capable of generating image data suitable for tracking motion based on emissions in the visible or invisible regions of the electromagnetic spectrum, such as visible light or infrared. Further, sensors 180 can include sensors configured to monitor the usage of system resources, including, without limitation, main processor 140, GPU 170 or memory 160.

Although FIG. 1 illustrates one example of a device 100 for implementing contextually aware determination of respiration rate, various changes may be made to FIG. 1. For example, the device 100 could include any number of components in any suitable arrangement. Similarly, according to certain embodiments, device 100 may be one of multiple devices (for example, a smartphone and a smartwatch) used for performing contextually aware determination of respiration rate. In general, devices including computing and communication systems come in a wide variety of configurations, and FIG. 1 does not limit the scope of this disclosure to any particular configuration. While FIG. 1 illustrates one operational environment in which various features disclosed in this patent document can be used, these features could be used in any other suitable system.

Figure 2:
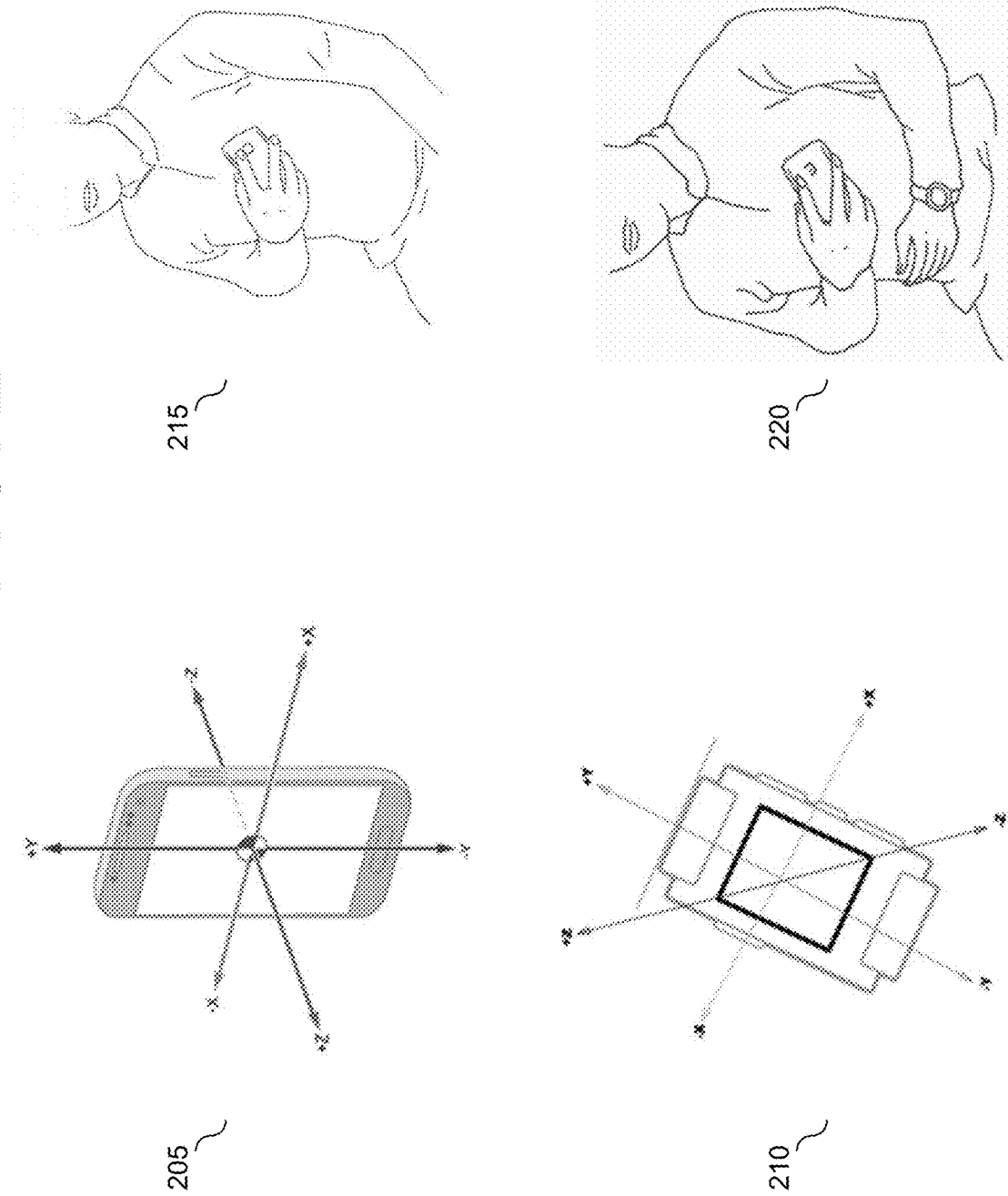
FIG. 2 illustrates examples of mobile devices measuring a subject's respiration rate according to various embodiments of this disclosure.

FIG. 2 illustrates examples of mobile devices measuring a subject's respiration rate according to various embodiments of this disclosure.

Respiration Rate ("RR"), otherwise known as breaths per minute, along with oxygen saturation ($SpO_2$) are important indicators of cardiopulmonary health in both healthy people, and patients with Chronic Obstructive Pulmonary Disease (COPD) or asthma. At the same time, healthy individuals as well as patients with cardiopulmonary conditions often carry smartphones and other multi-sensor apparatus (for example, tablets and smartwatches). Accordingly, embodiments according to this disclosure provide systems and methods for obtaining clinically useful estimates of a subject's respiration rate through commonly carried apparatus (for example, a smartphone), thereby making doctors and patients less reliant on specialized and/or hospital-specific equipment (for example, pneumotachographs or Respitrace bands) to obtain RR data.

Referring to the non-limiting example of FIG. 2, an electronic device, such as a smartphone 205, or a smart watch 210, of device 100 in FIG. 1, includes a suite of sensors configured to obtain data regarding the condition of the device. Such sensors might include inertial measurement units (IMU's) (such as accelerometers, gyroscopes, magnetometers, etc.) capable of detecting the motion of the device along 3 or more axes. The on-board sensors of smartphone 205 and smart watch 210 may further include a global positioning unit, a microphone, a thermometer, and in some cases, a red LED PPG sensor. Additionally, smartphone 205 and smart watch 210 may be operating as platforms for wellness software which can request and receive patient data over a network. The on-board sensor technology provided in smartphone can be used to collect one or more sets of data associated with a user's pulmonary activity, such as by a user 215 holding smartphone 205 over his or her chest, or by a user 220 holding smartphone 205 over his chest and smart watch 210 over his abdomen.

The technical challenges associated with determining a clinically useful estimate of a user's respiration rate from devices such as smartphone 205 and smart watch 210 include, without limitation, the reliability and noisiness of the data obtained by the devices' sensors that can greatly vary across variations in measurement context. For example, microphone data may, in certain contexts, such as when the user is indoors, be a good source of data associated with a user's pulmonary activity, but an unreliable source of data in other contexts, such as when the user is outdoors or moving. Similarly, the types of noise found in IMU data may vary according to the user's posture (such as when a user is lying down), or other contextual factors, such as whether a user is moving.

Given that the reliability of the sensor data and nature of the noise found in sensor data associated with a user's respiratory activity can vary across contexts, the challenges associated in obtaining a clinically useful estimate of a user's respiration rate from sensor data also include selecting appropriate sources of sensor data and appropriate algorithms for processing the sensor data to extract respiratory signals from noise. Embodiments according to this disclosure enhance the performance of devices (for example, smartphones and smart watches) as tools for on-demand or continuous measurement of user's respiration rates by performing contextually-aware selection of sources of sensor data and contextually-aware selection of algorithms for determining a user's respiration rate.

Figure 3:
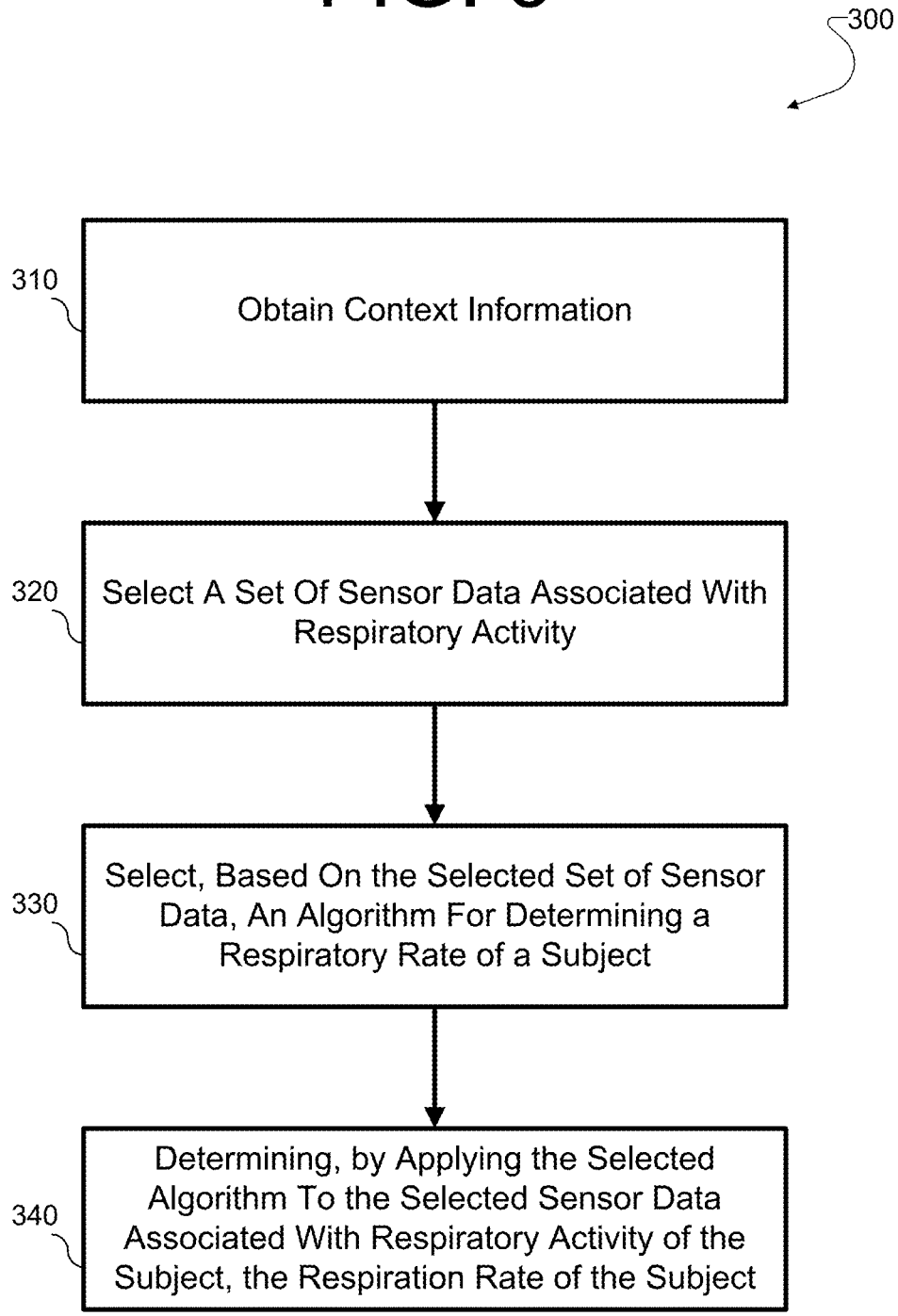
FIG. 3 illustrates operations of a method for performing a contextually aware determination of a subject's respiration rate according to certain embodiments of this disclosure.

FIG. 3 illustrates operations of a method 300 for performing a contextually aware determination of a subject's respiration rate according to certain embodiments of this disclosure.

Referring to the non-limiting example of FIG. 3, while the operations of method 300 are described according to embodiments in which a single electronic device (for example device 100 in FIG. 1) collects the sensor data and performs the recited operations, the present disclosure is not so limited. Embodiments, wherein sensor data is collected across multiple devices (for example, a smartphone and a smart watch) or wherein the recited selection and determination steps are performed across multiple computing platforms (for example, a backend server and a client application running on a user device) are contemplated as being within the scope of the present disclosure.

Referring to the non-limiting example of FIG. 3, method 300 includes operation 310, wherein the electronic device obtains context information. As used in the present disclosure, the term "context information" encompasses information regarding the state of the device and subject whose respiration rate is to be measured which affects the accuracy and/or feasibility of estimating the subject's respiration rate.

Device context information or information regarding the state of the device includes, without limitation, audio data, image data (for example, lighting conditions, image(s) of surroundings, etc.), location information, information regarding the position of the electronic device in relation to the subject, and/or orientation of the electronic device. From such device context information, aspects of the condition of the device which are relevant to the accuracy and feasibility of a respiration rate measurement (for example, is the device in a noisy location, making use of the microphone difficult? or is the device oriented at an angle from which it is difficult to obtain movement data from a subject's chest?). Device context information can also include information regarding the operation of the electronic device as a portable computing platform. Such information includes, without limitation, the amount of charge left in a battery, whether a BLUETOOTH® connection to another sensor-enabled device is present, and consumption of system resources by other programs and processes running on the electronic device. For example, information indicating that the device's battery is low, or that another application is using most of the device's memory, may indicate that a respiration rate determination using a computationally intensive algorithm is not possible, or likely to exhaust the battery.

Subject context information, or information regarding the subject includes, without limitation, medical history information (for example, information showing the subject has a damaged or deformed lung), a determination of a subject's posture (for example, sitting, standing or prone), time (for example, did the subject just wake up?), an estimate of clothing worn by the subject (for example, material, thickness, etc.) and/or information regarding the subject's current activity level (for example, are they exercising or getting ready for bed?).

In certain embodiments according to this disclosure, context information regarding both the device and the subject is obtained explicitly, by sensors on the electronic device, or implicitly, by various combinations thereof. As used in this disclosure, explicitly obtaining information encompasses the electronic device requesting the context from a source. Examples of the electronic device explicitly obtaining context information include, without limitation, presenting an interface (for example, an interactive survey, asking the subject questions such as "Did you just wake up?" or "Is it hard to breathe today?"), or downloading contextual information, such as medical history information, or environmental information (for example, meteorological or air quality information) from a host computer.

Context information can, according to certain embodiments, be obtained directly from sensor data. For example, a PPG sensor on an electronic device can directly obtain an $SpO_2$ value for the subject. Similarly, an audio level from a microphone can provide contextual information as to whether the ambient sound level is too high for a microphone based measurement. As a further, non-limiting example, sensor data from a gyroscope and/or an IMU can indicate whether the device is suitably oriented for performing a respiration rate measurement.

Additionally, in some embodiments, context information can be implicitly obtained, or inferred from sensor data or explicitly obtained information. For example, an electronic device may explicitly obtain a user's home address (for example, through a form or by download) and in conjunction with global positioning system information, implicitly determine that the user is at home.

Additionally, in some embodiments, context information may be determined based on the application of a learnt model to data associated with respiratory activity of a subject. For example, a learnt model can be used to train the electronic device to recognize whether an electronic device is correctly oriented on a subject's chest by generating and learning, at least one template of a representative ballistocardiogram (BCG) signal of the user from captured accelerometer data from at least one axis via a training phase. According to certain embodiments, the electronic device can segment subsequently obtained accelerometer data into chunks similar to the template signal to check similarity between the template and the real-time accelerometer data to determine context information as to whether the electronic device is correctly oriented on the subject's chest. Embodiments in which an electronic device utilizes a learnt model to obtain context information include embodiments where the electronic device utilizes a learnt model to resolve whether the device is positioned on the subject's chest or abdomen, whether the subject is wearing heavy clothes, and embodiments where the electronic device uses a trained model to estimate a distance between the device and the subject's mouth are possible and within the contemplated scope of this disclosure. Such learnt model(s) can be built through supervised, semi-supervised or un-supervised machine learning, including deep learning involving neural networks.

In some embodiments, obtaining context information can include detecting events of clinical interest, such as the lapse of a timer between respiratory rate measurements, or receiving information regarding events of cardiopulmonary interest, such as high air temperatures or emergencies (for example, a fire, or volcanic eruption).

In certain embodiments, the electronic device performing method 300 is capturing, via sensors provided in the electronic device, one or more sets of sensor data. In certain embodiments, the electronic device performing method 300 may also be receiving sensor data from a second electronic device, such as a smart watch paired with a smartphone. For example, a device may capture, over a given sample interval, IMU data, microphone data and PPG sensor data associated with respiratory activity of a subject. Further, the memory of the device may include program code, which when executed by a processor of the device, performs an algorithm for filtering and determining the respiration rate from a particular set or particular sets of sensor data (for example, an algorithm for determining RR from audio data, or from a combination of audio data and smart watch IMU data). For higher measurement accuracy, certain embodiments can utilize one or more sets of sensor data from multiple devices placed on one or more parts of the user's body at the same time. For example, a smartphone can be placed on the chest and a smart watch coupled to the smart phone can be placed on the abdomen. Combinations of IMU data from these two devices may capture better breathing signals than the devices in isolation. The combination of IMU data can, in some embodiments, be a summation of the devices' signals. In fact, in certain embodiments, the electronic device may have multiple respiration rate determining algorithms, some of which may utilize different sets of sensor data.

According to various embodiments, at operation 320, the electronic device selects a set of sensor data associated with respiratory activity of the subject based on the context information. In some embodiments, the obtained context information may be used to exclude sources of sensor data which, based on the context, are expected to yield high error levels in the determined respiration rate. For example, if the context information indicates that the subject or device is outside, then sensor data from a microphone may be excluded. On the other hand, if the context information indicates that the subject is currently using the electronic device to conduct a phone call (implying that the device is close to the user's mouth), then sensor data from the microphone may be selected, on the assumption that the microphone is suitably positioned to pick up audio signals which can reliably be attributed to the subject's breathing.

Additionally, as part of operation 320, the electronic device may compare a quality metric (for example, signal strength or a dynamic range of a signal) against a threshold value as part of selecting one or more sets of sensor data. The threshold value may be learnt through a training phase where variation of subjects, variation of contexts, and variation of signal quality are carefully labelled to understand the dynamic range of the signal. According to certain embodiments, the selection of a set of sensor data may be performed by consulting a mapping table (or other suitable data structure) of contexts, estimated measurement error and the data requirements of a plurality of algorithms maintained in a memory of the electronic device. Table 1 below provides an illustrative example of such a mapping table.

TABLE 1

| 1$^{st}$ Context | 2$^{nd}$ Context | N$^{th}$ Context | Sensor Data Set(s) | Algorithm Set(s) | M.A.E. |
|---|---|---|---|---|---|
| Device on Chest | User Sitting | Silent | Accelerometer - Y axis. | Algorithm 1 (e.g., FFT) | 0.93 B.P.M. |
| Device on Abdomen | User Siting | Speech | Gyroscope Magnitude | Algorithm 1, Algorithm 3 | 1.59 B.P.M. |
| ... | ... | ... | ... | ... | ... |
| Device on Abdomen | User Supine | Silent | Gyroscope - X axis | Algorithm 2 (e.g., Zero-crossing) | 0.85 B.P.M. |
| Device on Chest | User Supine | Coughing | Accelerometer Magnitude | Algorithm 4 | 2.50 B.P.M. |

As shown in the non-limiting example of Table 1, certain embodiments of a mapping table maintain correlations between combinations of contexts, sensor data requirements, and estimates of the mean absolute error ("MAE") associated with combinations of contexts, sets of sensor data, and in some embodiments, specified algorithms for determining respiration rate.

In some embodiments, some or all of the operations of method 300 may be performed as an ongoing, or background process on the electronic device. To improve performance and/or support continuous monitoring of respiration rate, the electronic device may, at regular intervals, receive updated context information. In some embodiments, the electronic device may select the set of sensor data associated with respiratory activity of the subject by switching from one set of sensor data to another set of sensor data, based on the updated context information. In this way, the electronic device is able to move through the operations of method 300 seamlessly by pre-performing the determination of a set of sensor data associated with respiratory activity of the subject.

In certain embodiments, at operation 330, the electronic device selects, based on the selected set(s) of sensor data, an algorithm from a plurality of algorithms for determining a respiration rate of the subject. In the non-limiting example of FIG. 3, the selection of the algorithm may be performed by consulting a mapping table, such as Table 1, to identify, from the algorithms utilizing the selected sensor data, the algorithm with the lowest average error rate. According to certain embodiments, the mapping table is generated by a learnt model which may be trained wholly or in part by the electronic device. In some embodiments, the mapping table may be provided to the electronic device, and the electronic device applies the learnt model to update and tune the mapping table to account for subject-specific contextual variations (for example, a subject being a loud telephone speaker whose speaking levels drown out audio signals associated with her breathing).

In some embodiments, the selection of the algorithm from the plurality of algorithms for determining the respiration rate of the subject is triggered by a user-initiated respiration measurement request, such as clicking on a "measure respiration rate" button provided by the user interface of a health care application (for example, the SAMSUNG™ HEALTH application). According to some embodiments, the selection of the algorithm may be triggered, or performed in response to a change of a sensing mode of the electronic device. For example, the electronic device may be switched from an "on demand" to a continuous, or seamless measurement mode, wherein method 300 is performed as an ongoing, or background process on the electronic device, thereby obviating the need for the subject to remember when to measure her respiration rate.

As shown in the illustrative example of FIG. 3, at operation 340, the electronic device determines a value for the respiration rate of the subject by applying the selected algorithm to the selected sensor data associated with the respiratory activity of the subject. In some embodiments, the electronic device may select from a set of algorithms which includes, for various sets of inputted sensor data, algorithms for determining respiration rate based on a time-domain analysis, algorithms for determining respiration rate based on a frequency-domain analysis, and algorithms for determining respiration rate using a total variation (TV) filter. Additionally, other algorithms, such as algorithms incorporating $SpO_2$ measurement data or algorithms which de-noise sensor data using other processing techniques, such as a Kalman filter, are possible and within the contemplated scope of this disclosure.

As a non-limiting example of certain embodiments according to this disclosure, a time domain algorithm for determining respiration rate includes the steps of: 1.) receiving accelerometer sensor data (for example accelerometer data collected on the z-axis); 2.) applying a low-pass filter to smooth the data; 3.) detrending the data; 4.) removing motion artifacts; 5.) interpolating the sensor data to fill in gaps, such as with a cubic spline; 6.) detecting peaks in the signal; and 7.) determining a respiration rate from the interval(s) between peaks.

Figure 4:
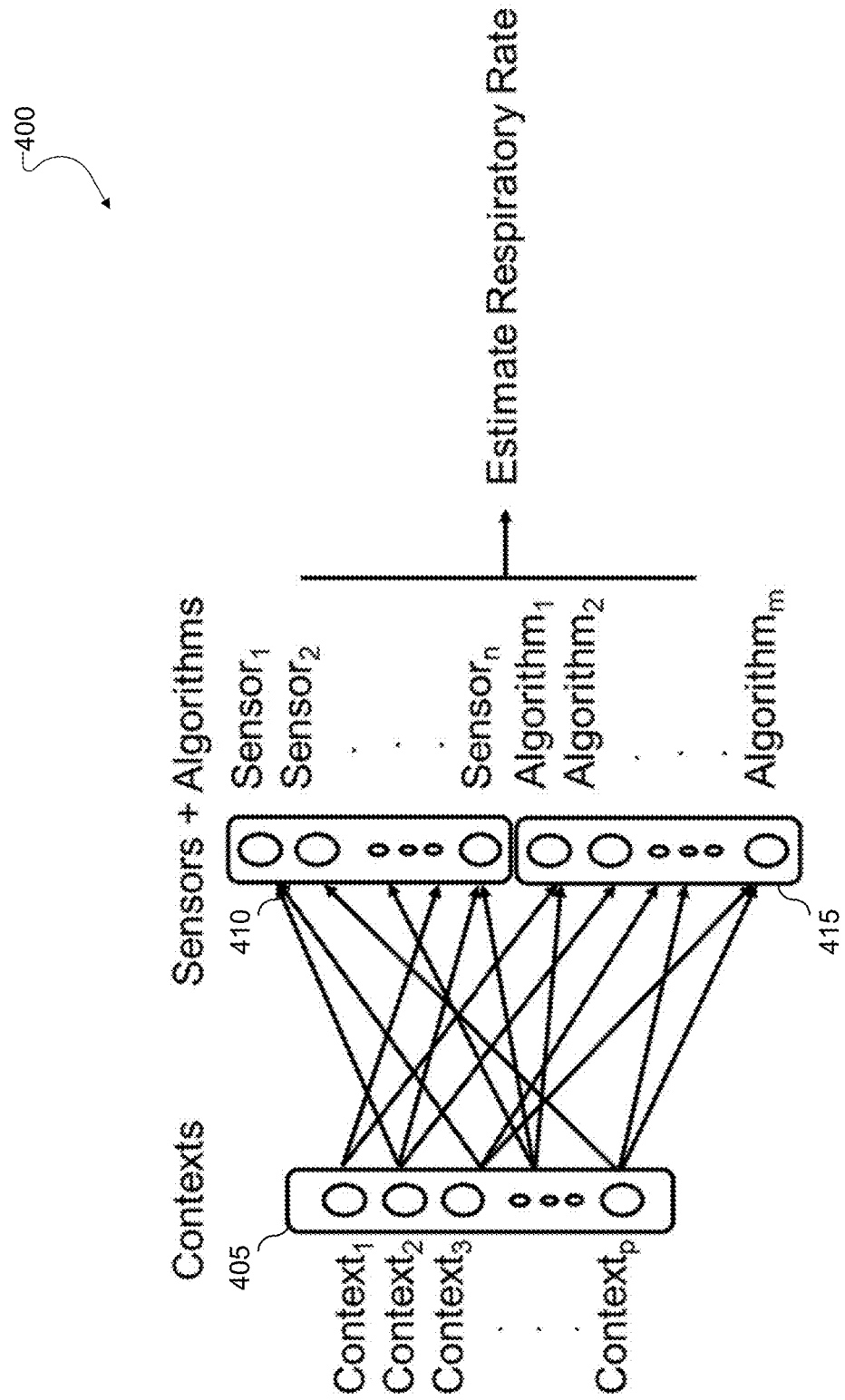
FIG. 4 illustrates combinations of contexts, types of sensor data, and algorithms for determining a subject's respiration rate based on one or more learnt models, according to certain embodiments of this disclosure.

FIG. 4 illustrates combinations of contexts, types of sensor data, and algorithms for determining a subject's respiration rate based on one or more learnt models according to certain embodiments of this disclosure.

Referring to the non-limiting example of FIG. 4, for a given electronic device, the full set of potential ways 400 of determining the respiration rate of a subject is dependent on the sizes of a set of determined contexts 405, the superset 410 of sets of sensor data available to the electronic device, and a set of algorithms 415 for performing a respiration rate measurement. Depending on the sizes of each of sets 405, 410 and 415, the number of members in the full set 400 could be potentially very large. Further, some of the possible combinations of contexts, sets of sensor data and algorithms may present unacceptably high error rates, and thus be of limited clinical value.

Thus, the technical challenges associated with implementing context-aware measurement on an electronic device include training a model, generating a mapping or otherwise generating control logic for the electronic device to select one or more set(s) of sensor data and at least one measurement algorithm that yields a clinically acceptable error rate.

In the illustrative example of FIG. 4, set of contexts 405 comprises contexts numbered 1-p. Similarly, the superset 410 of sets of measurement data comprises sets of sensor data numbered 1-n, and the set of algorithms 415 comprises algorithms numbered 1-m. In this non-limiting example, the arrows from members of set of contexts 405 to members of sensor data superset 410 and set of algorithms 415 represent combinations of sensor data and algorithms provided to the electronic device (for example, as part of a table, such as TABLE 1), which can be used by the electronic device to select sensor data (for example, in operation 320 of FIG. 3) and an algorithm (for example, in operation 330 of FIG. 3). Attention is directed to the fact that not every permutation of context, sensor data and algorithm is shown as linked by arrows, reflecting the fact that certain combinations of contexts, sets of sensor data, and algorithms do not yield results with clinically acceptable error profiles.

Figure 5:
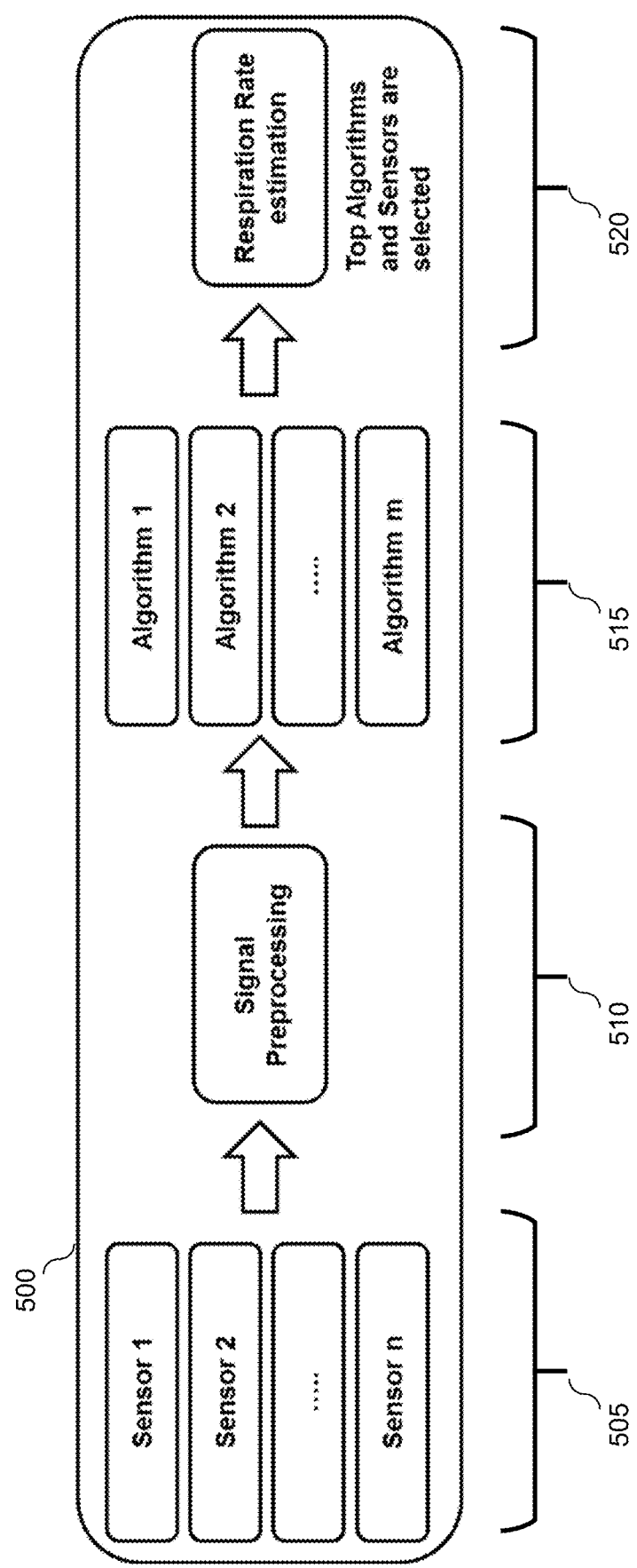
FIG. 5 illustrates aspects of a method for determining and mapping combinations of contexts, types of sensor data, and algorithms for determining a subject's respiration rate using devices according to some embodiments of this disclosure.

FIG. 5 illustrates aspects of a method for determining and mapping clinically acceptable combinations of contexts, types of sensor data, and algorithms for determining a subject's respiration rate using devices according to some embodiments of this disclosure. In one embodiment, this method is carried out during the training phase.

According to certain embodiments, combinations of algorithms and sensor data which yield results with clinically acceptable error profiles are determined on a context-by-context basis. FIG. 5 depicts a processing workflow 500 for determining the best performing combination of sensor data and algorithms for a particular context (or a particular combination of contexts, such as shown in FIG. 1).

Referring to the non-limiting example of workflow 500, at operation 505, sets of sensor data associated with respiratory activity of a subject numbered 1-n are captured from sensors of the electronic device during a set interval. In some cases, the sets of sensor data numbered 1-n may correspond to all of the sets of sensor available to the electronic device. In other cases, sets of sensor data numbered 1-n may comprise a subset of the sets of sensor data available to the electronic device, as certain sets of data can be excluded in advance (for example, microphone data in a context with large amounts of ambient noise). A ground truth value of the subject's respiration rate during the set interval is obtained using a trusted sensor, such as a pneumotachograph.

In some embodiments according to this disclosure, at operation 510, signal pre-processing is performed on each set of sensor data. Such signal pre-processing may comprise applying a low pass filter (LPF) to the sensor data or interpolating the sensor data.

According to the non-limiting example of FIG. 5, at operation 515, the processed sets of data are fed to each of the algorithms numbered 1-m to obtain, at operation 520, m separate values of the estimated (as determined by each of the algorithms) respiration rate of the subject. At operation 520, each of the estimated values of the subject's respiration rate is compared against the ground truth value of the subject's respiration rate, to obtain error rates. From this the top-performing combinations of algorithms and sensors can be identified and mapped to a table or other data structure from which an electronic device can select, for a particular context, an appropriate set of sensor data and an appropriate algorithm.

Figure 6:
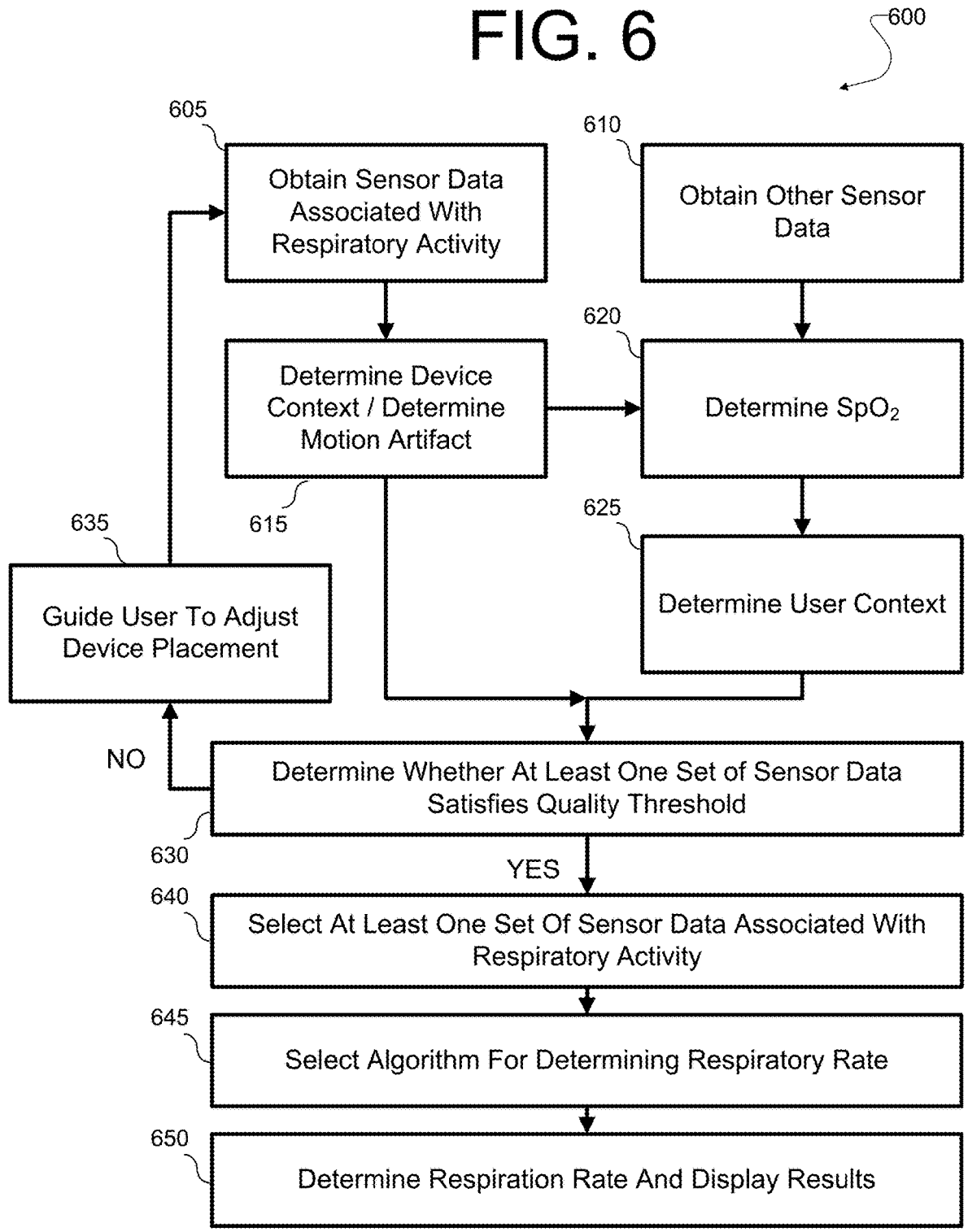
FIG. 6 illustrates operations of a method for performing a context aware respiration rate determination according to some embodiments of this disclosure.

FIG. 6 illustrates operations of a method 600 for performing a context aware respiration rate determination according to some embodiments of this disclosure. As shown in this illustrative example, the operations of a method for determining respiration rate according to certain embodiments of this disclosure can obtain data not directly associated with respiratory activity of the subject, and can apply a learnt model to guide the user to adjust the position of the electronic device to better capture sensor data associated with respiratory activity.

Referring to the non-limiting example of FIG. 6, at operation 605, the electronic device obtains sensor data associated with respiratory activity. Sensor data may be obtained via sensors incorporated in the electronic device (for example, electronic device 100 in FIG. 1), including, without limitation, microphones, cameras, and IMUs.

In certain embodiments, at operation 610, the electronic device obtains other sensor data, or sensor data not directly associated with respiratory activity of the subject, for example, oxygen saturation levels, or the subject's heart rate. In some embodiments, the electronic device obtains the other sensor data from sensors provided in the electronic device, such as, for example a red LED sensor for performing PPG measurements. In some embodiments, the electronic device obtains other sensor data from sensors not included in the electronic device, including, without limitation, sensors in a smart watch, or in a heart rate monitor on the subject's finger or chest.

In the non-limiting example of FIG. 6, at operation 615, the electronic device determines, based on the sensor data, the device context. For example, at operation 615, the electronic device may determine, through the application of a learnt model developed by comparing sensor data (for example, gyroscope data along an axis of particular interest, such as the z-axis) associated with the subject's respiration, whether the device is correctly oriented. In addition to whether the device is correctly oriented for a motion based measurement (for example, tracking the rise and fall of the chest or abdomen), device context which may be determined at operation 615 includes, without limitation, the distance of the microphone from the user's mouth, which may, in certain embodiments, be inferred from the device angle, audio level data, and knowledge regarding the user (for example, height, or other proxy for arm length).

Also, in some embodiments, the electronic device may determine and remove motion artifacts from the sensor data. For example, certain inertial measuring units (IMUs) are susceptible to "drift" or providing sensor data due to calibration errors, rather than in response to actual motion of the sensor. At operation 615, the electronic device may process the sensor data to remove such artifacts.

According to certain embodiments, at operation 620, the device determines based on the other sensor data, a value of a datum which is relevant to a determination of user context. According to some embodiments, the electronic device determines the datum linked to user context based on a combination of the other sensor data and the device context. In the non-limiting example of FIG. 6, the electronic device determines the subject's $SpO_2$ level, which can be a useful datum for determining aspects of the user's context (including, for example, whether the user exhibits signs of chronic obstructive pulmonary disease).

At operation 625, the device determines. based on at least one of the sensor data associated with the subject's respiratory activity, the determined device context, the other sensor data, or the determined datum linked to user context, the user's context. For example, at operation 625, the electronic device may determine that the user's context fits into one or more categories of posture state (for example, seated, supine, and standing, etc.), affective state (for example, agitated, calm, and attentive, etc.) and/or physiological state (for example, hungry, tired, dizzy or stressed).

In certain embodiments according to this disclosure, at operation 630, the measuring device performs a check to determine whether at least one set of sensor data associated with respiratory activity satisfies a quality threshold. For example, at operation 630, the electronic device may determine that a set of sensor data is collected from a sensor which was placed at an angle that is within the range of angles from which a reliable measurement may be obtained. As another example, the electronic device may determine that a sensor data exhibits a sufficiently great dynamic range or sufficiently large signal size.

In the non-limiting example of FIG. 6, if at operation 630, the electronic device determines that there is not at least one set of sensor data associated with respiratory activity which satisfies a quality threshold, method 600 proceeds to operation 635, wherein the electronic device provides the user with a notification, such as a request to change an aspect of the device or user contexts. For example, in some embodiments, at operation 635, the electronic device displays a screen or plays a message requesting that the user adjust the device placement. In some embodiments, the device provides the user with a message or a screen asking them to change a user context, such as by switching from a seated to a supine posture. Subsequent to operation 635, method 600 reverts to operation 605 to re-attempt the determination of respiration rate.

If, at operation 630, it is determined that at least one set of sensor data satisfies a quality threshold, then method 600 proceeds to operation 640, wherein the electronic device selects, based on the determined context information, at least one set of sensor data associated with the subject's respiratory activity, and which satisfies the quality threshold. The determination performed at operation 640 may be performed based on device context information (for example, device context determined at operation 615), user context (for example, user context determined at operation 625), or a combination thereof.

According to some embodiments, at operation 645, the electronic device selects an algorithm for determining the respiratory rate of the subject based on the selected set of sensor data. In certain embodiments, the selection of the algorithm at operation 645 is performed based on the selected set of sensor data and other information, such as context information. The determination performed at operation 645 may be performed based on a trained mapping (for example, a mapping generated using workflow 500 in FIG. 5) or on a learnt model maintained and updated by the electronic device.

In certain embodiments according to this disclosure, at operation 650, the electronic device determines the subject's respiratory rate by applying the selected algorithm to the selected set(s) of sensor data and displays the result on a screen of the electronic device, or on a screen of another electronic device.

Figure 7:
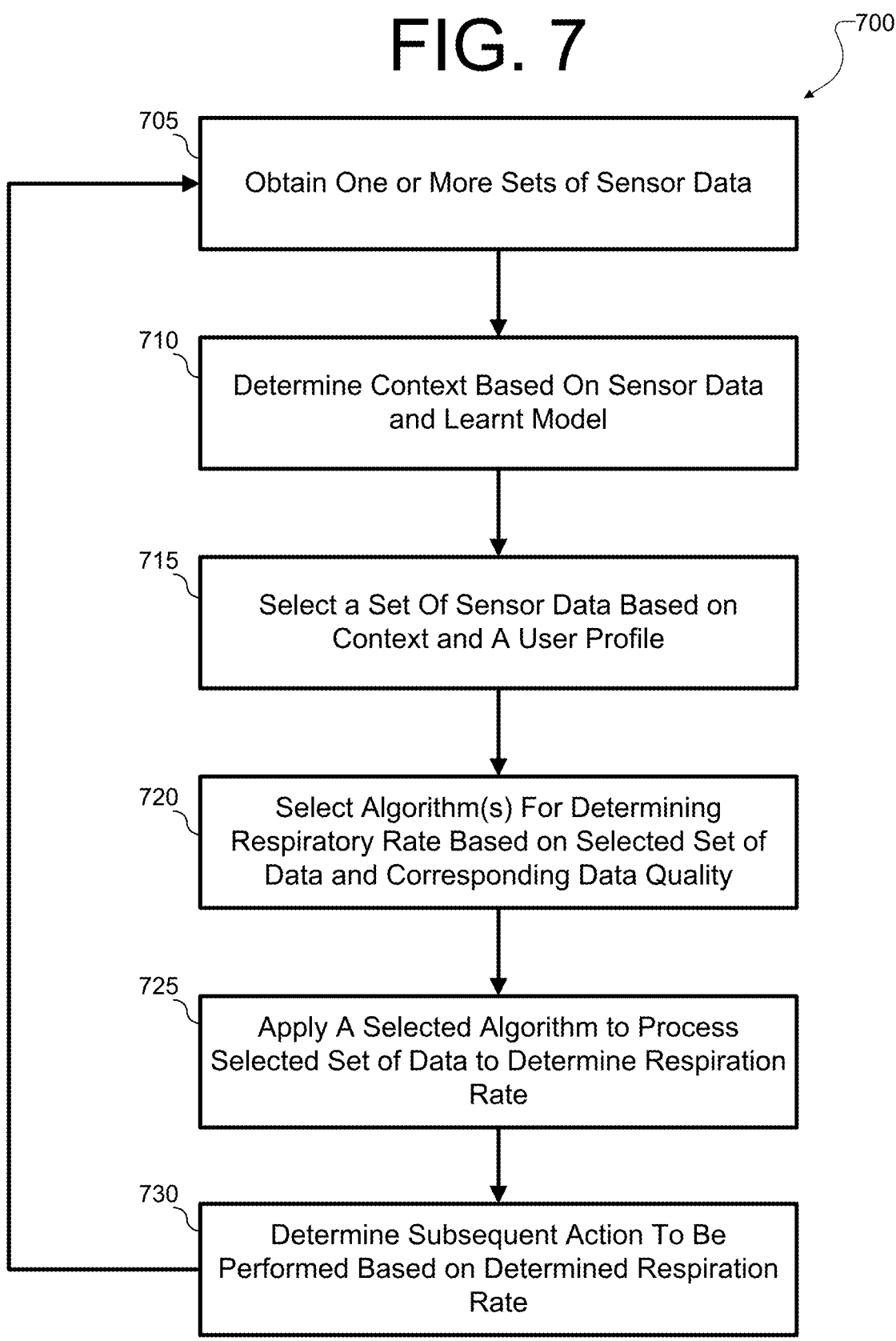
FIG. 7 illustrates operations of a method for monitoring a user's respiration rate in a selected measurement mode according to various embodiments of this disclosure.

FIG. 7 illustrates operations of a method 700 for monitoring a user's respiration rate in a selected measurement mode according to various embodiments of this disclosure. Electronic devices performing context-aware determination of respiration rate may operate in one or more measurement modes. As used in this disclosure, the term measurement mode encompasses a mode of operation of an electronic device characterized by, without limitation, the triggering of respiratory rate determinations, and the use of additional functionalities, such as sensor fusion and algorithm switching, such as discussed in connection with the example shown in FIG. 8 herein. Examples of measurement modes for determining respiration rate according to embodiments of this disclosure include "always-on" respiration rate measurement, "on demand" measurement, and "event triggered" measurement. According to certain embodiments, an electronic device may present a user interface allowing a subject to select a measurement mode. In some embodiments, the electronic device may switch automatically between measurement modes. For example, the electronic device may switch from an "always on" measurement mode to an "on-demand" measurement mode without user input in response to relevant context information (for example, a time value indicating that the subject is likely asleep, or an indication that the electronic device's battery is low).

Referring to the non-limiting example of FIG. 7, operations of a method 700 for determination of respiration rate while in an "always on" measurement mode are shown. According to certain embodiments, when an electronic device is in an "always on" measurement mode, the electronic device constantly monitors the subject's current context, and processes sensor data based on the context to complete the measurement. For example, if the electronic device determines that the subject is in an outdoor setting, based on sensor data such as GPS data, light and the time of day, a set of sensor data from the microphone may not be selected, based on a mapping of sensors to contexts, or a learnt model implemented by the electronic device. Instead, accelerometer measurements will be used while the electronic device continues to obtain context information indicating that the user is in an outdoor setting. However, in some embodiments, although the user is outdoors, sensor data from a microphone may still be collected to complete the measurement.

According to certain embodiments, at operation 705, the electronic device obtains one or more sets of sensor data, such as from electronic sensors provided on the electronic device itself, or on a device connected to the electronic device (for example, a heart rate or blood pressure measuring device). In the non-limiting example of FIG. 7, operation 705 may be performed by constantly or periodically monitoring sensor data from the sensors on the device, as well as the quality of data (for example, whether a quality value associated with the data exceeds a threshold value). In certain embodiments, monitoring the quality of the data may further comprise running multiple instances of a method for determining respiration rate, to determine the variance between algorithms, and whether any combinations of algorithms are yielding unforeseen errors (for example, returning impossibly high or low values of the subject's respiration rate).

In some embodiments, at operation 710, the electronic device determines a context (for example, a location of the subject, a time of day, a lighting condition, orientation or position of the electronic device, posture of the subject or activity of the subject holding the electronic device) based on the sensor data obtained at operation 715, which, depending on the contexts to be determined, is applied to one or more learnt models implemented by the electronic device. For example, while time of day data can be obtained directly, other context information, such as a user's posture, may be inferred from combinations of sensor data, such as a combination of device orientation and acceleration (or lack of acceleration). In some embodiments, at operation 710, the electronic device determines a specific combination of contexts, for example, "user sitting" and "device outdoors."

According to certain embodiments, at operation 715, the electronic device selects one or more sets of sensor data based on the determined context and user profile data in a memory of the electronic device. In the non-limiting example of FIG. 7, data maintained in the user profile may include data relating to medical conditions for which, if the determined respiratory rate is above or below a threshold value, an alert should be presented to the subject or a clinician. Data maintained in the user profile may also include information which may affect the selection of sensors, such as conditions associated with weak breathing. In some embodiments, the user profile data includes the subject's health record, disease history, medications taken, and information regarding a patient's present medical treatment.

In some embodiments, at operation 720, the electronic device selects at least one algorithms for determining respiratory rate based on the selected set(s) of sensor data and corresponding data quality. According to certain embodiments, including embodiments supporting a seamless switching, or sensor fusion mode of operation, the electronic device may, at operation 720, select multiple algorithms associated with multiple combinations of sensor data and context.

According to the non-limiting example of FIG. 7, at operation 725, the electronic device applies one of the selected algorithms to process a selected set of data to determine the subject's respiratory rate.

In certain embodiments according to this disclosure, at operation 730, responsive to determining the subject's respiratory rate, the electronic device determines one or more subsequent actions (for example, calling an emergency service, notifying a physician, presenting a reminder to "slow down," etc.). After determining one or more subsequent actions to be taken based on the determined respiration rate, method 700 loops back to operation 705.

Figure 8:
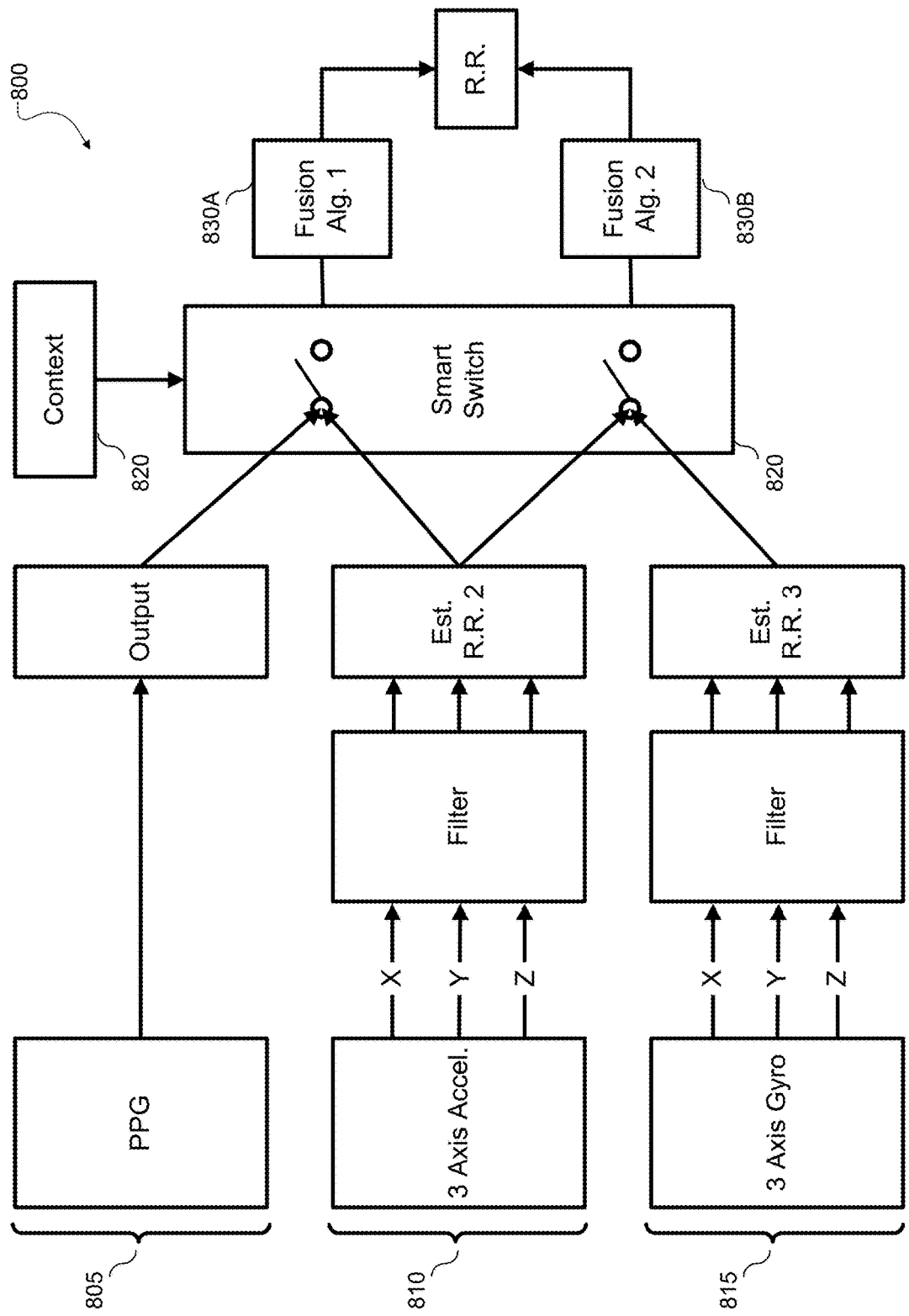
FIG. 8 illustrates aspects of a processing pipeline for providing seamless transitions across context changes when the device is in a continuous measurement mode according to certain embodiments of this disclosure.

FIG. 8 illustrates aspects of a processing pipeline 800 for providing seamless transitions across context changes when the device is in a continuous measurement mode, thereby enhancing the electronic device's ability to provide continuous respiration rate measurements. According to some embodiments, the operations for performing continuous monitoring of respiration rate are performed as a looped sequence of determinative steps, such as determining which set of data to use, and determining which algorithm to apply to the selected data. In some cases, changes in context require repeating certain determinative steps of the process, which can be demanding of system resources and cause latency issues.

In the non-limiting example of FIG. 8, processing pipeline 800 is structured to provide seamless transitions across contexts without interruption of a continuous measurement functionality caused by waiting for the processor to determine, for example which particular set of sensor to use for the current context. As shown in FIG. 8, processing pipeline introduces parallelism and smart switching to remove the selection of sets of sensor data as a source of discontinuity in providing a continuous respiration rate measurement functionality.

As shown in the illustrative example of FIG. 8, processing pipeline 800 includes three sensor data pipelines, comprising a pipeline 805 of data captured by a PPG sensor, a pipeline 810 of data captured by a three-axis accelerometer, and a pipeline 815 of data captured by a three-axis gyroscope. According to certain embodiments, there may be more or fewer than three sensor data pipelines. In the non-limiting example of FIG. 8, the set of sensor pipelines comprises all of the sensors which can provide sensor data or context associated with measurement of a subject's respiratory rate.

According to certain embodiments, pipeline 805 provides PPG sensor information, and outputs values of $SpO_2$ levels, which can be used as part of a respiration rate measurement.

In some embodiments, pipeline 810 captures sensor data from each of the three measurement axes of a three-axis accelerometer. The captured data is filtered by one or more filters appropriate for the sensor data (for example, a low-pass filter), and pre-processed to output a cleaned-up, or processed set of sensor data associated with the subject's respiration rate.

In certain embodiments, pipeline 815 captures sensor data from each of the three measurement axes of a three-axis gyroscope. The captured data is filtered by one or more filters appropriate for the sensor data (for example, a Kalman filter), and pre-processed to output a second cleaned-up, or otherwise processed set of sensor data associated with the subject's respiration rate.

As shown in the non-limiting example of FIG. 8, the outputs of each of sensor data pipelines 805, 810 and 815 are fed into a smart switch 820 which facilitates the seamless implementation of continuous respiration rate measurement across contexts by receiving periodic updates of context data and, based on the context data, feeding the outputs of sensor data pipelines 805, 810 and 815 to one of a plurality of fusion algorithms 830 A & B for final processing of the sensor pipeline data to obtain a determination of the subject's respiration rate.

According to certain embodiments, first fusion algorithm 825A is an algorithm which utilizes a first set of sensor data from sensor data pipelines 805-815, and second fusion algorithm 825B is an algorithm which uses a second set of sensor data from sensor data pipelines 805-815. In such cases, when smart switch receives updated context information, the operation of selecting sensor data associated with the subject's respiration rate in response to the context change comprises switching from the first set of sensor data to the second set of sensor data. Accordingly, the efficiency and seamlessness of operation of the electronic device can be enhanced by queueing, or connecting to the smart switch, fusion algorithms associated with expected contexts, so that the step of selecting sensor data comprises a simple switch, rather than a separate determination of which sensor data to use. In some embodiments, first fusion algorithm 830A and second fusion algorithm 830B may comprise the same underlying operations, but differ in that one version may be more accurate, while the other version of the algorithm may be more computationally efficient.

Figure 9:
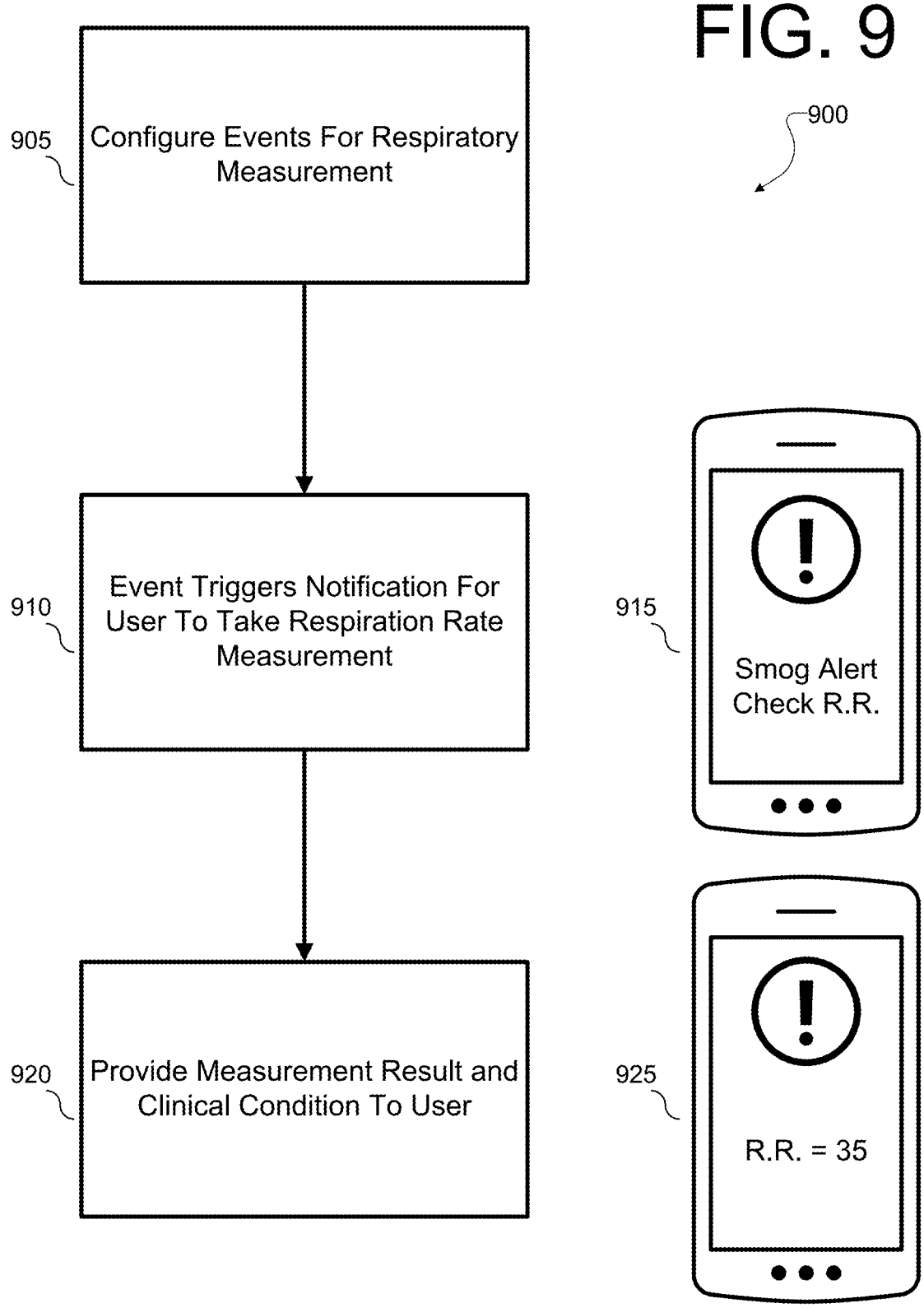
FIG. 9 illustrates operations of a method for performing contextually-aware respiration rate measurement while operating in an event-triggered measurement mode according to certain embodiments of this disclosure.

FIG. 9 illustrates operations of a method 900 for performing contextually-aware respiration rate measurement while operating in an event-triggered measurement mode according to certain embodiments of this disclosure.

As discussed above, certain electronic devices according to this disclosure support multiple measurement modes, including, without limitation, "on-demand" and continuous measurement modes (as shown, for example in FIGS. 7 & 8). In an event-triggered measurement mode, the electronic device presents the subject with a notification to perform a respiration rate measurement in response to the occurrence of a configured event.

Referring to the non-limiting example of FIG. 9, method 900 includes operation 905, wherein the electronic device receives configuration information of events triggering a notification to perform a respiration rate measurement. Depending on embodiments, the configuration information can be configured by clinicians or by patients based on their own preferences. Events which can trigger a notification include, without limitation, the lapse of a timer set at the most recent previous respiration rate measurement, crossing a threshold value of another metric of clinical interest (for example, heart rate, blood sugar or $SpO_2$), or an atmospheric event (for example, a volcanic eruption, smog warning, or fire in the vicinity).

In some embodiments, at operation 910, a configured event occurs, triggering a notification 915 for a user to perform a respiration rate measurement. In the non-limiting example of FIG. 9, the notification 915 may be provided through a screen of the electronic device, and provide text identifying the event and notifying the subject to perform a measurement. In some embodiments, the current time of the day can be an event to trigger the measurement. For example, preset times (for example, 8:00 a.m. and 8:00 p.m.) can be configurable events for triggering an alert to the user to perform a respiration rate measurement. In certain embodiments, the notification may be provided through a device other than the electronic device, such as a linked smart watch. In some embodiments, the notification may be provided via an email, an SMS, or other communication protocol.

Referring to the non-limiting example of FIG. 9, at operation 920, the electronic device performs a contextually-aware respiration rate measurement according to various embodiments of this disclosure and provides the measurement result 925 to the user. According to some embodiments, measurement result 925 may be provided with additional information, such as information recommending action to be taken by the subject, or, as shown in FIG. 9, information providing clinical context regarding the result. In the non-limiting example of FIG. 9, a warning icon is shown above the respiration rate value of 35 breaths per minute, indicating that the subject is hyperventilating or otherwise breathing unusually rapidly.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle.

What is claimed is:

1. A method for contextually aware determination of respiration rate, the method comprising:
    receiving, by an electronic device, sensor data from at least one sensor of the electronic device in response to the electronic device being placed next to a chest or an abdomen of a subject;
    determining, by the electronic device, context information associated with at least one of a state of the electronic device or a state of the subject, wherein the context information comprises a suitability of an orientation of the electronic device that is determined by applying a first learnt model to the sensor data;
    selecting, by the electronic device, a set of the sensor data associated with respiratory activity of the subject, based on the context information;
    selecting, by the electronic device, an algorithm from a plurality of algorithms for determining a respiration rate of the subject, wherein the algorithm is selected by applying a second learnt model to the context information and the selected set of the sensor data;
    determining, by the electronic device by applying the selected algorithm to the selected set of the sensor data associated with respiratory activity of the subject, the respiration rate for the subject;
    updating, by the electronic device, the second learnt model based on the determined respiration rate; and
    displaying, by the electronic device, the determined respiration rate on a display of the electronic device.

2. The method of claim 1, wherein the context information further comprises at least one of audio data, image data, a determination of a posture of the subject, location information, medical history information of the subject, or a combination thereof.

3. The method of claim 1, further comprising:
    obtaining, by the electronic device, updated context information; and
    selecting, by the electronic device, the set of the sensor data associated with respiratory activity of the subject by switching to the set of the sensor data from another set of sensor data, based on the updated context information.

4. The method of claim 3, wherein selecting the algorithm from the plurality of algorithms for determining the respiration rate is performed in response to at least one of a user-initiated respiration measurement request, a change of sensing mode of the electronic device or a combination thereof.

5. The method of claim 1, wherein a portion of the selected set of the sensor data associated with respiratory activity of the subject is obtained from a second electronic device.

6. The method of claim 1, wherein the context information further comprises medical history information of the subject.

7. The method of claim 1, further comprising:
determining, by the electronic device, a subsequent action to be performed based on the determined respiration rate.

8. An apparatus comprising:
a processor;
one or more sensors coupled to the processor, configured to capture one or more sets of sensor data; and
a memory, containing computer-readable program code, which when executed by the processor, causes the apparatus to:
receive sensor data from at least one of the one or more sensors in response to the apparatus being placed next to a chest or an abdomen of a subject;
determine context information associated with at least one of a state of the apparatus or a state of the subject, wherein the context information comprises a suitability of an orientation of the apparatus that is determined by applying a first learnt model to the sensor data;
select a set of the sensor data associated with respiratory activity of the subject, based on the context information;
select an algorithm from a plurality of algorithms for determining a respiration rate of the subject, wherein the algorithm is selected by applying a second learnt model to the context information and the selected set of the sensor data;
determine, by applying the selected algorithm to the selected set of the sensor data associated with respiratory activity of the subject, the respiration rate for the subject;
update the second learnt model based on the determined respiration rate; and
display the determined respiration rate on a display of the apparatus.

9. The apparatus of claim 8, wherein the context information further comprises at least one of audio data, image data, a determination of a posture of the subject, location information, medical history information of the subject, or a combination thereof.

10. The apparatus of claim 8, wherein the memory contains computer-readable program code, which when executed by the processor, causes the apparatus to:
obtain updated context information, and
select the set of the sensor data associated with respiratory activity of the subject by switching to the set of the sensor data from another set of sensor data, based on the updated context information.

11. The apparatus of claim 10, wherein the memory contains computer-readable program code, which when executed by the processor, causes the apparatus to select the algorithm from the plurality of algorithms for determining the respiration rate in response to at least one of a user-initiated respiration measurement request, a change of sensing mode of the apparatus or a combination thereof.

12. The apparatus of claim 8, wherein a portion of the selected set of the sensor data associated with respiratory activity of the subject is obtained from a second apparatus.

13. The apparatus of claim 8, wherein the context information further comprises medical history information of the subject.

14. The apparatus of claim 8, wherein the memory contains computer-readable program code, which when executed by the processor, causes the apparatus to:
determine a subsequent action to be performed based on the determined respiration rate.

15. A non-transitory computer-readable medium comprising program code, which when executed by a processor, causes an apparatus to:
receive sensor data from at least one sensor of the apparatus in response to the apparatus being placed next to a chest or an abdomen of a subject;
determine context information associated with at least one of a state of the apparatus or a state of the subject, wherein the context information comprises a suitability of an orientation of the apparatus that is determined by applying a first learnt model to the sensor data;
select a set of the sensor data associated with respiratory activity of the subject, based on the context information;
select an algorithm from a plurality of algorithms for determining a respiration rate of the subject, wherein the algorithm is selected by applying a second learnt model to the context information and the selected set of the sensor data;
determine, by applying the selected algorithm to the selected set of the sensor data associated with respiratory activity of the subject, the respiration rate for the subject;
update the second learnt model based on the determined respiration rate; and
display the determined respiration rate on a display of the apparatus.

16. The non-transitory computer-readable medium of claim 15, wherein the context information further comprises at least one of audio data, image data, a determination of a posture of the subject, location information, medical history information of the subject, or a combination thereof.

17. The non-transitory computer-readable medium of claim 15, further comprising program code, which when executed by the processor, causes the apparatus to:
obtain updated context information, and
select the set of the sensor data associated with respiratory activity of the subject by switching to the set of the sensor data from another set of sensor data, based on the updated context information.

18. The non-transitory computer-readable medium of claim 17, further comprising program code, which when executed by the processor, causes the apparatus to select the algorithm from the plurality of algorithms for determining the respiration rate in response to at least one of a user-initiated respiration measurement request, a change of sensing mode of the apparatus or a combination thereof.

19. The non-transitory computer-readable medium of claim 15, wherein the context information further comprises medical history information of the subject.

20. The non-transitory computer-readable medium of claim 15, further comprising program code, which when executed by the processor, causes the apparatus to:
   determine a subsequent action to be performed based on the determined respiration rate.

\* \* \* \* \*